US011602357B2

(12) United States Patent
Sweeney et al.

(10) Patent No.: US 11,602,357 B2
(45) Date of Patent: Mar. 14, 2023

(54) DRILL BIT WITH DELIVERY DEVICE FITTING AND METHOD OF USE THEREOF

(71) Applicant: Spinal Generations, LLC, Mokena, IL (US)

(72) Inventors: Patrick J. Sweeney, Flossmoor, IL (US); Matthew V. Leyden, St. Paul, MN (US)

(73) Assignee: Spinal Generations, LLC, Mokena, IL (US)

( * ) Notice: Subject to any disclaimer, the term of this patent is extended or adjusted under 35 U.S.C. 154(b) by 81 days.

(21) Appl. No.: 16/801,968

(22) Filed: Feb. 26, 2020

(65) Prior Publication Data

US 2020/0187960 A1 Jun. 18, 2020

Related U.S. Application Data

(63) Continuation-in-part of application No. 29/696,644, filed on Jun. 28, 2019, now Pat. No. Des. 926,321, which is a continuation of application No. 29/673,291, filed on Dec. 13, 2018, now Pat. No. Des. 926,320.

(51) Int. Cl.
*A61B 17/16* (2006.01)

(52) U.S. Cl.
CPC ...... *A61B 17/1615* (2013.01); *A61B 17/1697* (2013.01)

(58) Field of Classification Search
CPC ............ A61B 17/1655; A61B 17/1615; A61B 17/1635; A61B 17/1637; A61B 17/1697; A61B 17/8802; A61B 17/8805
See application file for complete search history.

(56) References Cited

U.S. PATENT DOCUMENTS

| D242,428 | S | 11/1976 | Morris |
| D358,212 | S | 5/1995 | Sullivan |
| D362,720 | S | 9/1995 | Holmen et al. |
| 5,456,267 | A * | 10/1995 | Stark .................... A61B 10/025 606/65 |
| D366,115 | S | 1/1996 | Sullivan |
| D378,314 | S | 3/1997 | Koros et al. |
| D390,956 | S | 2/1998 | Sjostrom et al. |
| 6,186,712 | B1 | 2/2001 | Senzaki |
| D441,448 | S | 5/2001 | Kumar |
| D449,504 | S | 10/2001 | Boyle et al. |
| D574,958 | S | 8/2008 | Schendel et al. |
| D606,196 | S | 12/2009 | Fares et al. |
| D614,941 | S | 5/2010 | Murphy |
| D637,289 | S | 5/2011 | Berberich |
| D652,929 | S | 1/2012 | Sibhatu et al. |

(Continued)

FOREIGN PATENT DOCUMENTS

GB 9 006 574711-0001 6/2019

*Primary Examiner* — Matthew J Lawson
(74) *Attorney, Agent, or Firm* — Foley & Lardner LLP

(57) ABSTRACT

A device for drilling into bone includes a luer portion having a luer thread. A bit portion is rigidly coupled to the luer portion, the bit portion configured to be detachably coupled to a bit driver. An adapter portion is rigidly coupled to the bit portion. A drilling portion is rigidly coupled to the adapter portion, the drilling portion comprising a flute configured to create a hole in the bone. A channel extends through the luer portion, the bit portion, the adapter portion, and the drilling portion.

12 Claims, 4 Drawing Sheets

(56) References Cited

U.S. PATENT DOCUMENTS

| | | | |
|---|---|---|---|
| D666,298 S | 8/2012 | Sibhatu et al. | |
| D706,893 S | 6/2014 | Diederich | |
| D710,175 S | 8/2014 | Moss et al. | |
| D732,669 S | 6/2015 | Fisler et al. | |
| D744,106 S | 11/2015 | Voudouris | |
| D773,926 S | 12/2016 | Sweeney et al. | |
| D801,796 S | 11/2017 | Sweeney et al. | |
| D803,038 S | 11/2017 | Baker et al. | |
| D803,039 S | 11/2017 | Karlsson | |
| D828,153 S | 9/2018 | Sato | |
| D830,820 S | 10/2018 | Sweeney | |
| D831,475 S | 10/2018 | Sweeney et al. | |
| D831,476 S | 10/2018 | Sweeney et al. | |
| D836,976 S | 1/2019 | Reese et al. | |
| D837,047 S | 1/2019 | Lin | |
| D882,085 S | 4/2020 | Sweeney et al. | |
| 2005/0107800 A1* | 5/2005 | Frankel | A61B 17/1655 606/92 |
| 2009/0228012 A1* | 9/2009 | Gangji | A61B 17/3472 606/80 |
| 2010/0036381 A1* | 2/2010 | Vanleeuwen | A61B 17/8805 606/80 |
| 2011/0054537 A1* | 3/2011 | Miller | A61B 17/7044 606/279 |
| 2011/0056166 A1 | 3/2011 | Bartlett | |
| 2011/0112436 A1* | 5/2011 | Jones | A61B 10/025 600/567 |
| 2011/0257691 A1 | 10/2011 | Sutterlin et al. | |
| 2012/0035670 A1 | 2/2012 | Jackson et al. | |
| 2012/0143266 A1 | 6/2012 | Jackson et al. | |
| 2013/0060293 A1 | 3/2013 | Jackson et al. | |
| 2014/0309641 A1 | 10/2014 | Bourque et al. | |
| 2018/0243018 A1* | 8/2018 | Lintula | A61F 2/4225 |
| 2020/0038646 A1* | 2/2020 | Sweeney | A61B 17/864 |
| 2020/0187960 A1 | 6/2020 | Sweeney et al. | |

* cited by examiner

DRILL BIT WITH DELIVERY DEVICE FITTING AND METHOD OF USE THEREOF

CROSS-REFERENCE TO RELATED APPLICATIONS

This application is a continuation-in-part of U.S. Design patent application Ser. No. 29/696,644, filed Jun. 28, 2019, which is a continuation of U.S. Design patent application Ser. No. 29/673,291, filed Dec. 13, 2018, each of which is incorporated by reference herein in its entirety.

BACKGROUND

The present invention relates generally to the field of surgical tools and implements, and more particularly to devices and methods for drilling into and delivering substances to the interior of bones. The present invention further relates to devices and methods for removing material from the interior of a bone.

SUMMARY OF THE INVENTION

The embodiments described herein allow delivery of a substance (e.g., medication) to the internal of a bone. Furthermore, the embodiments described herein allow drilling into a bone and delivering substance to the internal of the bone using a single device. The devices and methods described herein also allow material to be removed from the interior of a bone.

One embodiment of the invention relates to a bone drilling device that includes a luer portion including a luer thread. A bit portion is rigidly coupled to the luer portion, the bit portion configured to be detachably coupled to a bit driver. An adapter portion is rigidly coupled to the bit portion. A drilling portion is rigidly coupled to the adapter portion, the drilling portion comprises a flute configured to create a hole in the bone. A channel having an open proximal end and an open distal end extends entirely through the luer portion, the bit portion, the adapter portion, and the drilling portion.

Another embodiment of the invention relates to a method for drilling into bone and delivering a substance to bone that includes inserting a guidewire into a bone. The method further includes providing a device for drilling into bone and delivering a substance to bone. The bone drilling device includes a luer portion including a luer thread. A bit portion is rigidly coupled to the luer portion, the bit portion configured to be detachably coupled to a bit driver. An adapter portion is rigidly coupled to the bit portion. A drilling portion is rigidly coupled to the adapter portion, the drilling portion comprises a flute configured to create a hole in the bone. A channel having an open proximal end and an open distal end extends entirely through the luer portion, the bit portion, the adapter portion, and the drilling portion. The method further includes coupling a bit driver to the bit portion, placing the channel over the guidewire, rotating the bit driver to rotate the bone drilling device, wherein the rotating the bone drilling device causes the drilling portion to drill into the bone, removing the guidewire from the bone and the bone drilling device, coupling a substance deliver device to the luer portion, and introducing the substance from the substance delivery device into the bone through the channel.

Another embodiment of the invention relates to a method for drilling into bone and taking a biopsy that includes inserting a guidewire into a bone. The method further includes providing a device for drilling into bone. The bone drilling device includes a luer portion including a luer thread. A bit portion is rigidly coupled to the luer portion, the bit portion configured to be detachably coupled to a bit driver. An adapter portion is rigidly coupled to the bit portion. A drilling portion is rigidly coupled to the adapter portion, the drilling portion comprises a flute configured to create a hole in the bone. A channel having an open proximal end and an open distal end extends entirely through the luer portion, the bit portion, the adapter portion, and the drilling portion. The method further includes coupling the bit driver to the bit portion, placing the channel over the guidewire, rotating the bit driver to rotate the bone drilling the device, wherein rotating the bone drilling device causes the flute to drill into the bone, advancing the bone drilling device into the bone further than the guidewire to obtain a biopsy sample of biopsy material, removing the bone drilling device and the guidewire from the bone, and plunging the bone drilling device to expel the biopsy material.

BRIEF DESCRIPTION OF THE DRAWINGS

The disclosure will become more fully understood from the following detailed description, taken in conjunction with the accompanying figures, wherein like reference numerals refer to like elements, in which.

DETAILED DESCRIPTION

Figure 1:
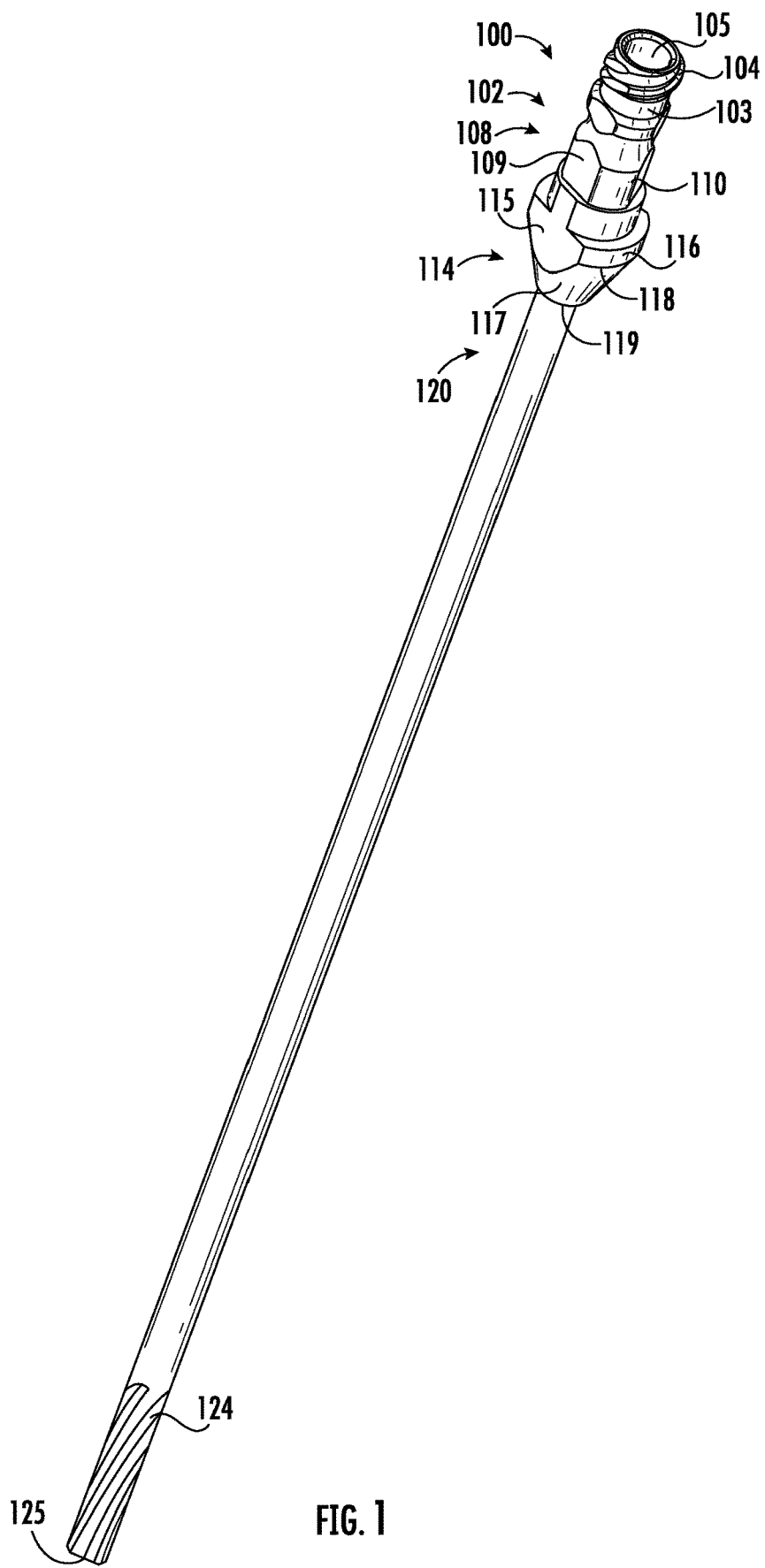
FIG. 1 is a perspective view of a bone drilling device according to a preferred embodiment.
Figure 2:
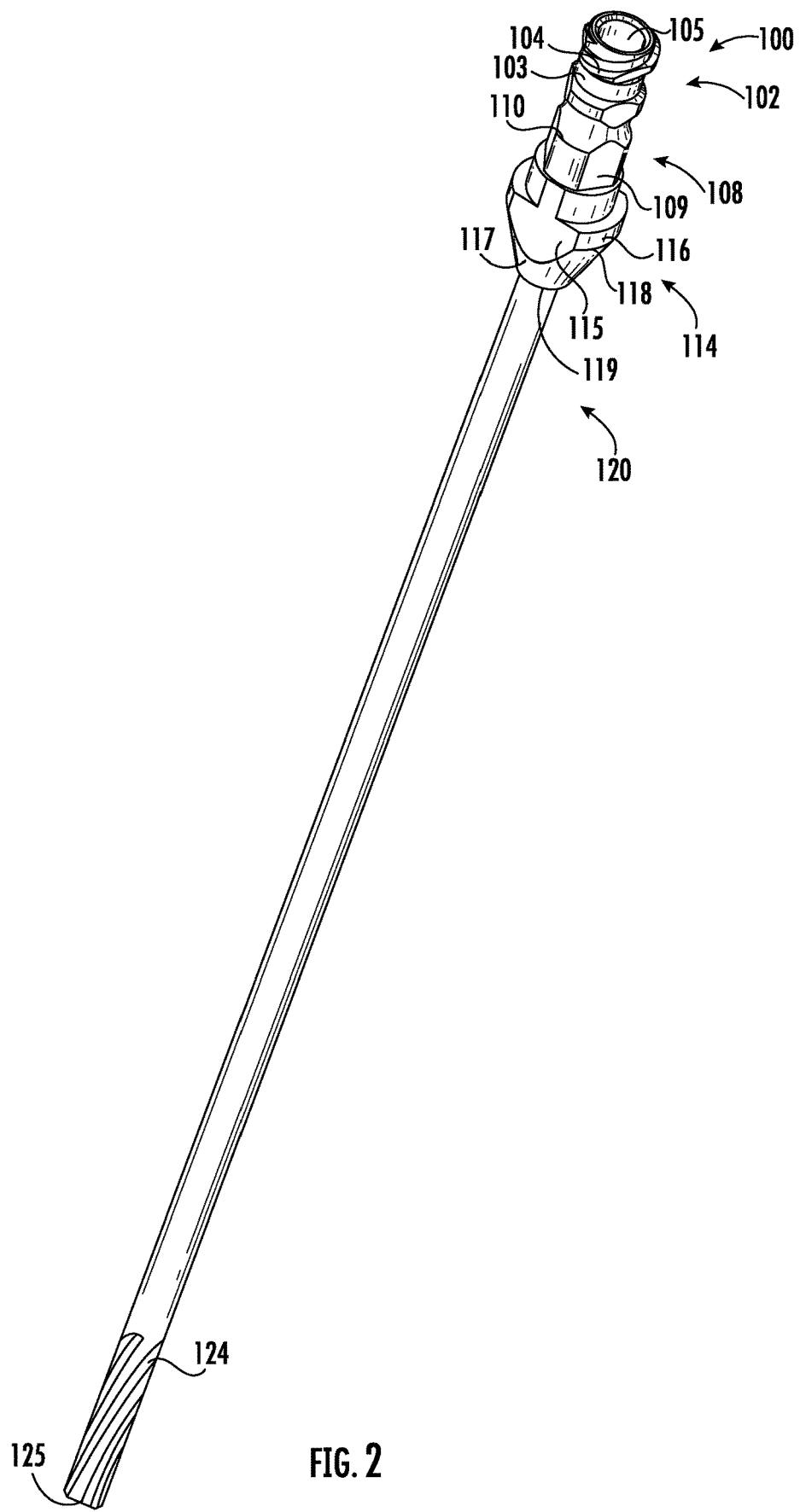
FIG. 2 is a second perspective view of the bone drilling device of FIG. 1.

FIGS. 1-2 are perspective views of a bone drilling device 100, according to a preferred embodiment. As shown, the bone drilling device 100 includes a luer portion 102, a bit portion 108, an adapter portion 114, and a drilling portion 120. In some embodiments, the luer portion 102, the bit portion 108, the adapter portion 114, and the drilling portion 120 may be a unitary device. In some embodiments, the luer portion 102, the bit portion 108, the adapter portion 114, and the drilling portion 120 can be individual components that are assembled during a manufacturing process. In some embodiments, at least two of the luer portion 102, the bit portion 108, the adapter portion 114, and the drilling portion 120 can be individual components that are assembled during a manufacturing process.

The bone drilling device 100 is preferably constructed from a metal (e.g., stainless steel, titanium, etc.), a biomaterial (e.g., polylactic acid and hydroxyapatite, etc.), a plastic (e.g., thermoplastic polymers, etc.), or a composite (e.g., carbon fiber reinforced plastics, etc.) capable of withstanding forces to which the bone drilling device 100 will be subjected to when drilling into a bone. In some embodiments, each of the luer portion 102, the bit portion 108, the adapter portion 114, and the drilling portion 120 may be constructed from the same material. In some embodiments, at least one of the luer portion 102, the bit portion 108, the adapter portion 114, and the drilling portion 120 can be constructed from different materials.

Figure 4:
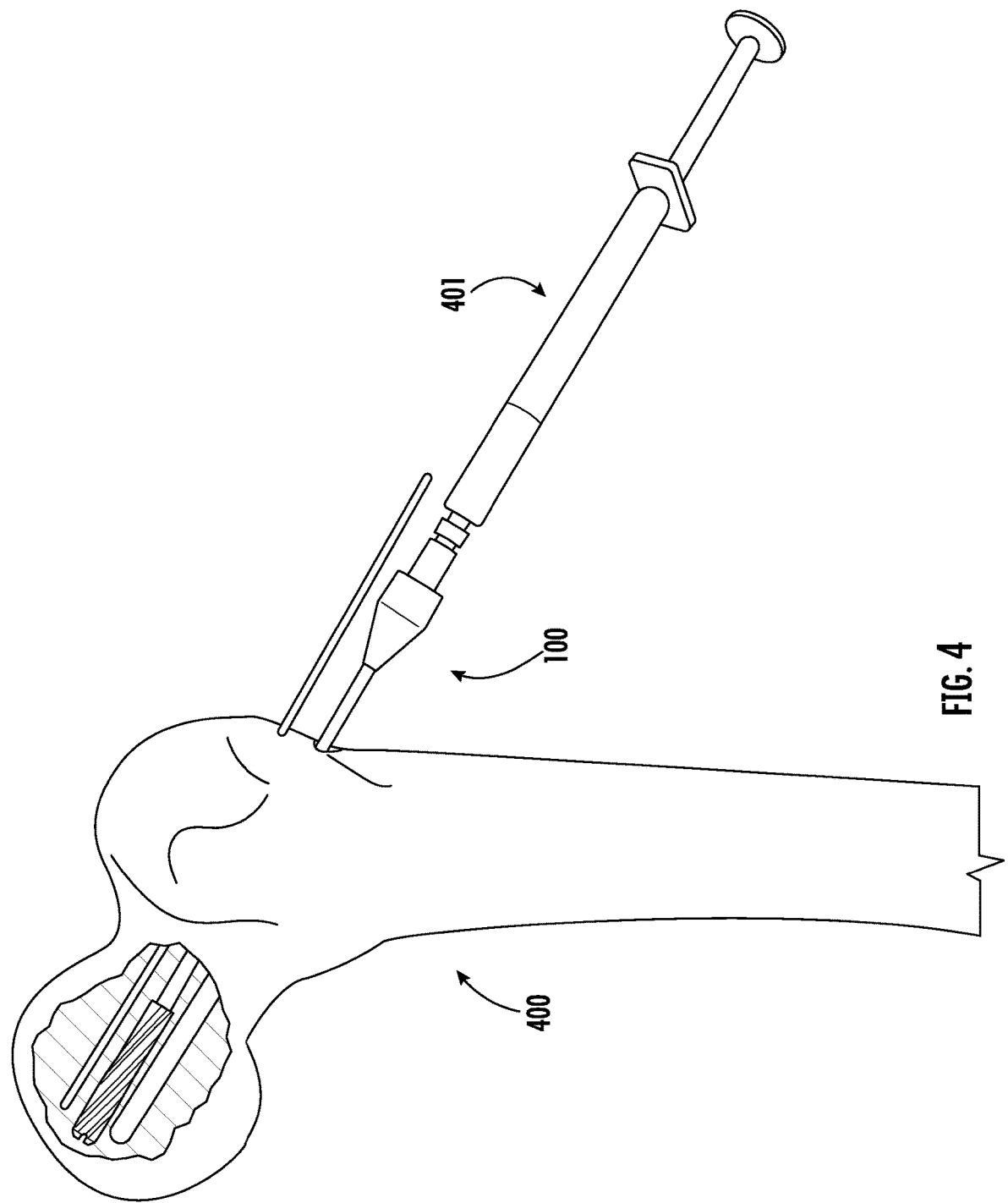
FIG. 4 illustrates a bone drilling device in a bone with a substance delivery device according to an exemplary embodiment.

The luer portion 102 is configured to receive a substance delivery device 401 (FIG. 4) and is shown to include a luer body 103, a luer thread 104, and a conduit 105. The luer body 103 is rigidly coupled to the bit portion 108 such that the luer body 103 and the bit portion 108 cannot rotate relative to each other. As shown, the luer portion 102 is a female luer. However, in some embodiments, the luer portion 102 can be a male luer.

In some embodiments, the luer body 103 can be a standard luer (e.g., the luer body 103 conforms to the 80369-7 standard of the International Standards Organization (ISO)). In some embodiments, the luer body 103 is customized to meet the needs of the procedure. For example, the luer body 103 may be longer or shorter than specified in the ISO standard. Additionally, the luer body 103 may include a diameter that is larger or smaller than specified by the ISO standard.

The luer body 103 defines the conduit 105 that extends entirely through the luer portion 102. As shown, the conduit 105 conforms to the ISO standard (e.g., the proximal end of conduit 105 may be an internal luer taper configured to receive a luer slip that conforms to the ISO standard). However, in some embodiments, the conduit 105 can be customized to be a different shape such that the conduit 105 can successfully receive a different connector.

The luer thread 104 extends from the luer body 103 and is configured to detachably couple to a connector that includes the appropriate mating thread (e.g., a matching male luer thread). As shown, the luer thread 104 partially extends around the circumference of the luer body 103. In some embodiments, the luer thread 104 can extend entirely around the circumference of the luer body 103.

The bit portion 108 is configured to be received by a rotational bit driver. The bit portion is rigidly coupled to the luer portion 102 such that there is no relative motion between the components. The bit portion 108 includes a flat bit face 109 that is substantially flat. In some embodiments, the bit portion 108 contains multiple flat bit faces 109. In an embodiment the flat bit faces 109 are configured into a hex bit 110. In an alternative embodiment the flat bit faces 109 are configured into other bit shapes (e.g., a square bit, an octagonal bit, a star-shaped bit, etc.). The outer diameter of the bit portion 108 is larger than the outer diameter of the luer portion 102 such that a rotational bit driver can fit around the luer portion 102 and engage the bit 108. In some embodiments, the bit portion 108 configured as the hex bit 110 is configured to be received by a hex bit driver. In other embodiments, the bit portion 108 is configured to be received by and used with a ¼ inch square drive that is altered with a modified luer fitting.

The adapter portion 114 is rigidly coupled to the bit portion 108 such that there is no relative motion between the components. The adapter portion 114 is configured to transition the bit portion 108 to the drilling portion 120 of the bone drilling device 100. The adapter portion is configured to couple to, or fit into, an adapter or handle, e.g., a Modified Zimmer Hall or an HMT adapter. The adapter portion 114 includes a flat adapter face 115, a curved adapter face 116, and a tapered section 117. The flat adapter face 115 is substantially flat. The curved adapter face 116 is substantially circular. In an alternative embodiment, the adapter portion 114 has a single continuous face. In an embodiment, the adapter portion 114 has a flat adapter face 115. In an embodiment, the adapter portion 114 has a curved adapter face 116. In an embodiment, the curved adapter face 116 is configured to have a diameter larger than that of the bit portion 108. In one embodiment the adapter has a plurality of flat adapter surfaces 115. In one embodiment at least one flat adapter face 115 is parallel to at least one flat bit face 109. In one embodiment at least one flat adapter face 115 is not parallel to at least one flat bit face 109. The tapered section 117 includes a proximal taper diameter 118 and a distal taper diameter 119. In some embodiments the proximal taper diameter 118 is larger than the distal taper diameter 119. In some embodiments the proximal taper diameter 118 is equal or substantially equal to the distal taper diameter 119. In some embodiments the proximal diameter 118 is equal to the diameter of the curved adapter face 116. In an embodiment, the tapered section 117 is configured such that the proximal taper diameter 118 is the largest diameter of the tapered section 117, and the distal taper diameter 119 is the smallest diameter of the tapered section 117. In some embodiments, the distal taper diameter 119 is substantially equal to the diameter of the drilling portion 120.

The drilling portion 120 is rigidly coupled to the adapter portion 114 such that there is no relative motion between the components. The drilling portion 120 includes a channel 121, the channel 121 having an open proximal end 122 and an open distal end 123, a flute 124, and a tip 125. In some embodiments the drilling portion 120 includes a plurality of flutes 124. The flute 124 is configured to create a hole in a bone or a plurality of holes. In some embodiments, the channel 121 and the tip 125 are configured to receive a biopsy sample.

Figure 3:
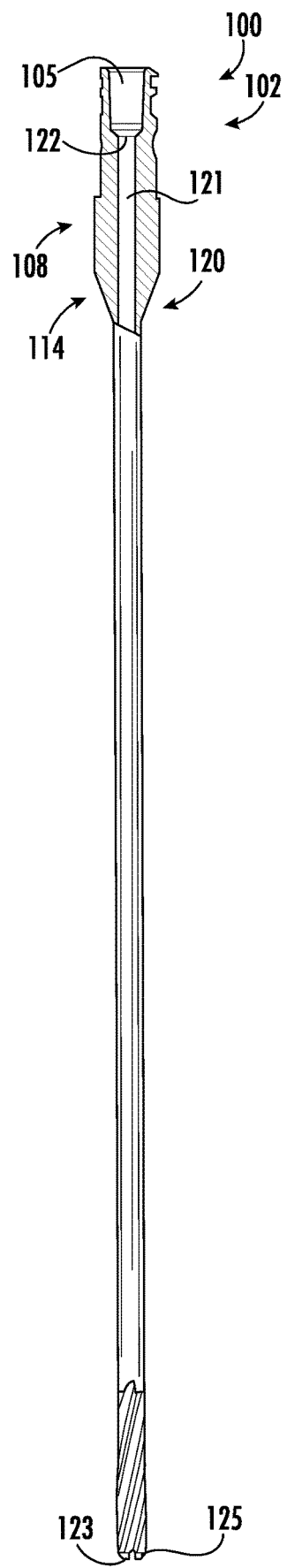
FIG. 3 is a cross-sectional view of the bone drilling device of FIG. 1.

A cross-sectional view of the bone drilling device 100 of FIG. 1, is shown in FIG. 3. The conduit 105 extends entirely through the luer portion 102, and partially into the bit portion 108. In some embodiments, the conduit 105 only extends through the luer portion 102. In some embodiments, the conduit 105 partially extends through the luer portion 102. In some embodiments, the conduit 105 fully extends into at least one of the luer portion 102, the bit portion 108, the adapter portion 114, and the drilling portion 120. In some embodiments the conduit 105 partially extends into at least one of the luer portion 102, the bit portion 108, the adapter portion 114, and the drilling portion 120.

The channel 121 is coupled to the conduit 105 so that they are in fluid communication. A substance can travel from the conduit 105, through an inlet portal at the open proximal end 122, and into the channel 121. In an embodiment, a substance can travel from the channel 121 through the open proximal end 122, and into the conduit 105. In an alternative embodiment, the channel 121 and the conduit 105 are a single canal. In an embodiment, the channel 121 is configured to receive a guidewire. In an embodiment, the conduit 105 is configured to receive a guidewire.

In operation, in one embodiment the user may desire to drill into a bone and deliver a substance to a bone using bone drilling device 100. The bone drilling device 100 may be used to create a hole in the bone and deliver substance to the bone.

The user first determines the appropriate insertion point for the bone drilling device 100 on the bone. The user then secures the bit portion 108 of the bone drilling device 100 to a rotational bit driver. The rotational bit driver is configured to fit around the luer portion 102 such that the luer portion 102 is not damaged when the rotational bit driver engages the hex bit 110. In some embodiments, the rotational bit driver can be magnetized such that the bit portion 108 is secured to the rotational bit driver without additional supporting structure. In other embodiments, the user secures the bit portion 108 in the rotational bit driver by hand.

With the bit portion 108 secured in the rotational bit driver, the user places the tip 125 on the insertion point and rotates the rotational bit driver. As the rotational bit driver rotates, the bit portion 108 rotates, thereby rotating the drilling portion 120 of the bone drilling device 100. The tip 125 rotates against the insertion point, and the tip 125 beings to bore a hole into the bone. As the rotational bit continues to rotate, the tip 125 extends deeper into the bone until the flute 124 on the drilling portion 120 contacts the bone. The flute 124 removes bone as the rotational bit driver continues to rotate, and the bone drilling device 100 extends deeper into the bone.

Once the bone drilling device 100 has drilled at least partially into bone, the rotational bit driver can be detached from bit portion 108, removing the rotational bit driver from the bone drilling device 100. The user may choose to deliver at least a substance (e.g. medication) to the interior of the bone. The user can fill a delivery device with a substance. The delivery device must be compatible with the luer portion 102 such that the delivery device can securely couple to the luer portion 102 and avoid leakage To inject the substance, the user secures the substance delivery device 401 to the luer portion 102. The user then injects the substance by forcing the substance from the substance delivery device 401, passing through the conduit 105, and into channel 121. The substance travels through the channel 121 to an outlet portal in the open distal end 123 of the drilling portion 120. The substance is delivered through the open distal end 123 to the bone. For example, in FIG. 4, the bone drilling device 100 is drilled into a bone 400, and a substance delivery device 401 is coupled to the bone drilling device 100. The substance delivery device 401 is configured to move a substance, such as bone void filler, bone cement, a flowable biologic, or other substances suitable for delivery to the bone, through the bone drilling device 100 and deliver the substance internally to the bone 400.

In an exemplary embodiment, the user may first insert a guidewire into the desired area before drilling into the bone 400. Placement of the guidewire may use a system for guidance (e.g., a fluoroscopic guidance system) to position the guidewire in the desired position. The guidewire may then serve as a guide for the bone drilling device 100. When using a guidewire the use places the guidewire through the open distal end 123 and into the channel 121 to guide the bone drilling device 100. In another embodiment, the bone drilling device 100 is used without a guidewire.

In an alternative embodiment, the substance delivery device 401 may also be used to remove substance (e.g., bone marrow or blood) from the internal of bone 400. A suction device may be coupled to the luer portion 102 to aid in the removal of material. Upon activating the suction device, material being removed from bone 400 travels through the channel 121 from the tip 125 and into the conduit 105.

The bone drilling device 100 may be used to both deliver substances to bone 400 and remove materials from the internal of a bone 400. In one embodiment, a user first uses the bone drilling device 100 to remove material from the interior of a bone 400. Next, the bone drilling device 100 is used to deliver substances to the areas within the bone 400. Alternatively, a user may first deliver a substance to the interior of bone 400 using the bone drilling device 100. After substance delivery, the user may remove excess substance (e.g., medication) or other materials (e.g. blood) by utilizing a suction device coupled to the luer portion 102 of the bone drilling device 100. In alternative embodiments the substance delivery device 401 or suction device may be coupled to the bone drilling device 100 via tubing or a delivery portal.

In operation, in an alternative embodiment, the user may desire to drill into a bone and take a biopsy sample. The bone drilling device 100 may be used to create a hole in a bone and be used as a biopsy trephine.

The user first determines the appropriate insertion point for the bone drilling device 100 on the bone. The user then secures the bit portion 108 of the bone drilling device 100 to a rotational bit driver. The rotational bit driver is configured to fit around the luer portion 102 such that the luer portion 102 is not damaged when the rotational bit driver engages the hex bit 110. In some embodiments, the rotational bit driver can be magnetized such that the bit portion 108 is secured to the rotational bit driver without additional supporting structure.

In an exemplary embodiment, the user may first insert a guidewire into the desired area before drilling into the bone. Placement of the guidewire may use a system for guidance (e.g., a fluoroscopic guidance system) to position the guidewire in the desired position. The guidewire may then serve as a guide for the bone drilling device 100. When a guidewire is used to drill into bone and take a biopsy sample, the bone drilling device 100 is drilled into the bone so that the tip 125 extends further into the bone, and past the guidewire, and collecting a sample of biological material in channel 121. The guidewire and the bone drilling device 100 are then removed from the bone. In some embodiments the guidewire is removed from the bone before the bone drilling device 100 is removed from the bone. In some embodiments the guidewire and the bone drilling device 100 are removed from the bone simultaneously or almost simultaneously. Once removed from the bone the bone drilling device 100 is plunged to expel the biopsy material from the bone drilling device 100. In some embodiments the guidewire is used to plunge the bone drilling device 100. In other embodiments, another device configured to be received by the conduit 105 and channel 121, is used to plunge the bone drilling device 100. In another embodiment, the bone drilling device 100 is used without a guidewire.

Various exemplary embodiments of the invention are described herein. Reference is made to these examples in a non-limiting sense. They are provided to illustrate more broadly applicable aspects of the invention. Various changes may be made to the invention described and equivalents may be substituted without departing from the true spirit and scope of the invention. In addition, many modifications may be made to adapt a particular situation, material, composition of matter, process, process act(s) or step(s) to the objective(s), spirit or scope of the present invention. Further, as will be appreciated by those with skill in the art, each of the individual variations described and illustrated herein has discrete components and features which may be readily separated from or combined with the features of any of the other several embodiments without departing from the scope or spirit of the present inventions. All such modifications are intended to be within the scope of claims associated with this disclosure.

The invention includes methods that may be performed using the subject devices. The methods may include the act of providing such a suitable device. Such provision may be performed by the end user. In other words, the "providing" act merely requires the end user obtain, access, approach, position, set-up, activate, power-up, or otherwise act to provide the requisite device in the subject method. Methods recited herein may be carried out in any order of the recited events that is logically possible, as well as in the recited order of events.

Exemplary aspects of the invention have been set forth above. As for other details of the present invention, these may be appreciated in connection with patents and publications generally known or appreciated by those with skill in the art. The same may hold true with respect to method-based aspects of the invention in terms of additional acts as commonly or logically employed by those with skill in the art.

In addition, though the invention has been described in reference to several examples optionally incorporating various features, the invention is not to be limited to that which is described or indicated as contemplated with respect to each variation of the invention. Various changes may be made to the invention described and equivalents (whether recited herein or not included for the sake of some brevity) may be substituted without departing from the true spirit and scope of the invention. In addition, where a range of values is provided, it is understood that every intervening value, between the upper and lower limit of that range and any other stated or intervening value in that stated range, is encompassed within the invention.

Also, it is contemplated that any optional feature of the inventive variations described may be set forth and claimed independently, or in combination with any one or more of the features described herein. Reference to a singular item, includes the possibility that there are plural of the same items present. More specifically, as used herein and in claims associated hereto, the singular forms "a," "an," "said," and "the" include plural referents unless specifically stated otherwise. In other words, use of the articles allow for "at least one" of the subject item in the description above as well as claims associated with this disclosure. It is further noted that such claims may be drafted to exclude any optional element. As such, this statement is intended to serve as antecedent basis for use of such exclusive terminology as "solely," "only" and the like in connection with the recitation of claim elements, or use of a "negative" limitation.

Without the use of such exclusive terminology, the term "comprising" in claims associated with this disclosure shall allow for the inclusion of any additional element—irrespective of whether a given number of elements are enumerated in such claims or the addition of a feature could be regarded as transforming the nature of an element set forth in such claims. Except as specifically defined herein, all technical and scientific terms used herein are to be given as broad a commonly understood meaning as possible while maintaining claim validity.

The breadth of the present invention is not to be limited to the examples provided and/or the subject specification, but rather only by the scope of claim language associated with this disclosure.

What is claimed is:

1. A device for drilling into bone, comprising:
   a luer portion comprising a luer thread, the luer portion extending along a longitudinal axis;
   a bit portion rigidly coupled to the luer portion, the bit portion configured to be detachably coupled to a bit driver;
   an adapter portion rigidly coupled to the bit portion, the adapter portion comprising a flat face and a curved face, the flat face extending along an axis parallel to the longitudinal axis of the luer portion and the curved face extending radially about the longitudinal axis of the luer portion, wherein a diameter of the curved face of the adapter portion is larger than a diameter of the bit portion;
   a drilling portion rigidly coupled to the adapter portion, the drilling portion comprising a flute, the flute configured to create a hole in the bone; and
   a channel having an open proximal end and an open distal end, the channel extending entirely through the luer portion, the bit portion, the adapter portion, and drilling portion.

2. The device of claim 1, wherein the channel is configured to receive a guidewire.

3. The device of claim 1, wherein the open proximal end is an inlet portal and the open distal end is an outlet portal.

4. The device of claim 3, wherein the inlet portal and the outlet portal are in fluid communication for continuous flow of a substance from the inlet portal to the outlet portal for delivery of the substance to the bone.

5. The device of claim 1, wherein the luer portion is configured to be detachably coupled to a substance delivery device.

6. The device of claim 5, wherein the substance delivery device is configured to deliver a flowable biologic.

7. The device of claim 5, wherein the substance delivery device is configured to deliver a bone void filler.

8. The device of claim 1, wherein the bit portion further comprises at least one hex bit configured to be detachably coupled to a hex bit driver.

9. The device of claim 1, wherein the adapter portion further comprises a tapered section.

10. The device of claim 1, wherein the device is configured to take a biopsy sample from the bone.

11. The device of claim 1, wherein the device is configured to remove substance from the interior of the bone.

12. The device of claim 1, wherein the flat face of the adapter portion is parallel to a flat face of the bit portion.

* * * * *